United States Patent
Feuersanger et al.

(10) Patent No.: US 6,477,430 B1
(45) Date of Patent: Nov. 5, 2002

(54) HANDS-FREE PADDLES USING SINGLE-USE ADHESIVE PADS

(75) Inventors: Robert A. Feuersanger, Andover, MA (US); Fred Borgenicht, Dover, MA (US); Karen Haas Bravo, Andover, MA (US); James Miller, Westford, MA (US); Anthony Matheson, Bedford, MA (US); Marc J. Zeitlin, Acton, MA (US); Daniel C. Canfield, Derry, NH (US); Curtis W. Freeman, Windham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/909,610

(22) Filed: Jul. 20, 2001

(51) Int. Cl.[7] .................................................. A61N 1/04
(52) U.S. Cl. ....................................................... 607/142
(58) Field of Search ................................ 600/382, 372, 600/391, 392; 607/142, 152, 148

(56) References Cited

U.S. PATENT DOCUMENTS 5,076,286 A   12/1991   Scharnberg
5,148,805 A   9/1992    Scharnberg
5,454,779 A   10/1995   Lurie et al.

OTHER PUBLICATIONS

"Heartstream Pads multifunction defibrillator electrods" Agilent Technologies, Jan. 2001.

*Primary Examiner*—Scott M. Getzow (57) ABSTRACT

A paddle for use with a defibrillator, the paddle being formed of an applicator attached to a pad portion. The applicator includes a flexible plate, a handle attached to a top of the flexible plate, and an applicator connector disposed on a bottom of the flexible plate. The pad portion is electrically connected to the applicator, and includes a flexible backing that is shaped by the flexible plate, a pad portion connector disposed on the flexible backing to form a connection to the applicator connector, a lid attached to the flexible backing, and an adhesive conductive medium attached to a bottom of the flexible backing and removably encased by the lid. An electrical contact is disposed on the lid and is electrically connected to the pad portion and is exposed while the conductive medium is removably encased by the lid.

34 Claims, 6 Drawing Sheets

HANDS-FREE PADDLES USING SINGLE-USE ADHESIVE PADS

BACKGROUND OF THE INVENTION

In general, defibrillation therapy is a process used to treat a patient experiencing heart fibrillation (i.e., where the heart experiences potentially fatal arrhythmias). The defibrillation process involves placing electrodes on the patient's chest and applying defibrillation shock. The defibrillation shock is a brief biphasic pulse of electricity to the cardiac muscle applied to the patient's bare chest to stimulate the heart and correct the fibrillation. The electrodes generally comprise an anode and a cathode, and come either as a single-use pads, or reusable paddles. The single-use pads are adhesive so as to adhere to the patient, and are thus hands-free. In contrast, the paddles do not adhere to the patient, and are therefore not hands-free.

In addition to providing defibrillation, cardiac defibrillators often provide caregivers with monitoring and additional therapy capabilities. Generally, a monitoring capability involves a passive use of the defibrillator to record signals generated by the patient. In contrast, a therapy capability involves injecting electricity or other signals into the patient. A monitoring capability often included in a defibrillator is electrocardiograph (ECG) monitoring. Therapy capabilities often included in a defibrillator include defibrillation, external cardiac pacing, and cardioversion with or without pacing. In order to perform the ECG monitoring, pacing, cardioversion including a pacing function, or defibrillation where the defibrillator indicates when a shock is to be applied, extended electrical contact needs to be made to the patient. This extended contact is provided using the single-use pads, or the reusable paddles to the extent this is possible. Further, extended contact is often more practical for other therapy and monitoring capabilities.

Figure 1:
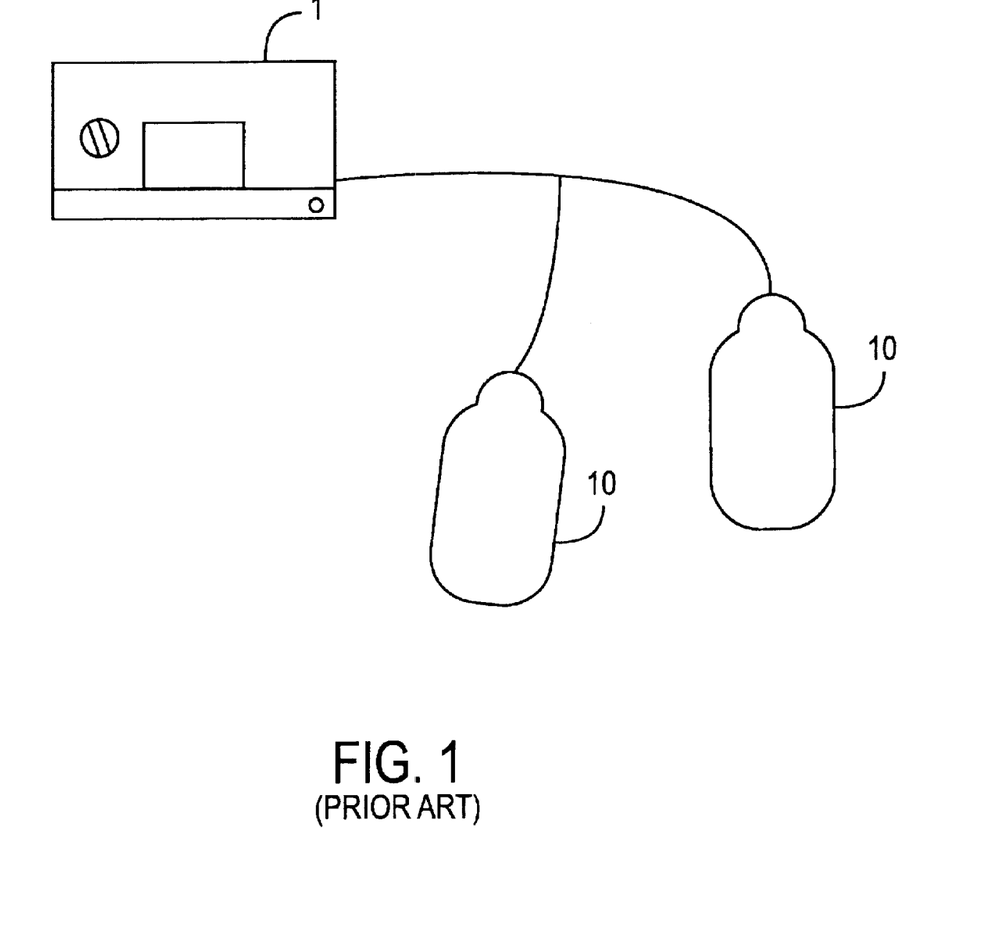
FIG. 1 shows a conventional defibrillation system using single-use pads.

FIG. 1 shows a defibrillation and monitoring system using self-adhesive, single-use pads 10. The defibrillator 1 is connected to the pads 10 by corresponding leads preconnected to the pads 10, and the pads 10 are then placed on the chest of the patient in predetermined positions. For defibrillation, the preferred location is for one pad 10 to be located on the upper-right sternal border of a chest of the patient, with one end near the clavicle and the other end just over the right nipple. The other pad 10 is located on the left side of the patient, wrapped from the back to the front under the left nipple and across the left midaxillary line. In this way, the pads 10 are placed to maximize current flow through the myocardium.

The pads 10 are generally constructed of a flexible metallic conductor plate sandwiched between a protective polymer backing and a conductive hydrogel adhesive that is used to adhere the pads 10 to the patient. The pads 10 also typically have a molded connector, or will have the leads molded into the pads 10, to connect corresponding leads to the defibrillator 1. An example of the pads 10 are the Heartstream pads produced by Agilent Technologies (part no. M3713A).

An advantage of single-use pads 10 is that the caregiver can adhere the pads 10 to the patient, and then administer the defibrillation shock without being in contact with the patient. This hands-free ability reduces the chance that the caregiver will be shocked by or otherwise exposed to the electrical pulse passing through the pads 10 during defibrillation. However, the pads 10 have drawbacks in that they are expensive to use, and they do not allow the caregiver to perform a quick look of the patient ECG in order to better assess the condition of the patient. A quick look generally is when a caregiver makes a temporary or abbreviated connection to the patient in order to obtain a quick reading of the patient's heart rhythm or condition. Specifically, if the caregiver wants to use the pads 10 to check a condition of the patient, the pads 10 must be removed from their protective packaging (not shown), causing the hydrogel to become dehydrated and contaminated and making them unsuitable for an additional use.

Figure 2A:
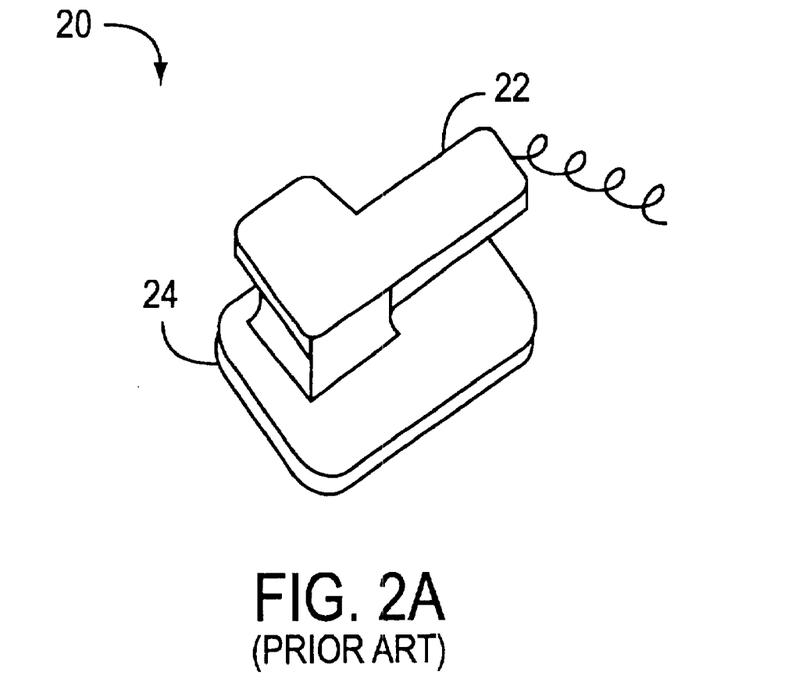
FIGS. 2A and 2B are schematic and bottom views of a conventional reusable paddle for use with the defibrillator of FIG. 1.
Figure 2B:
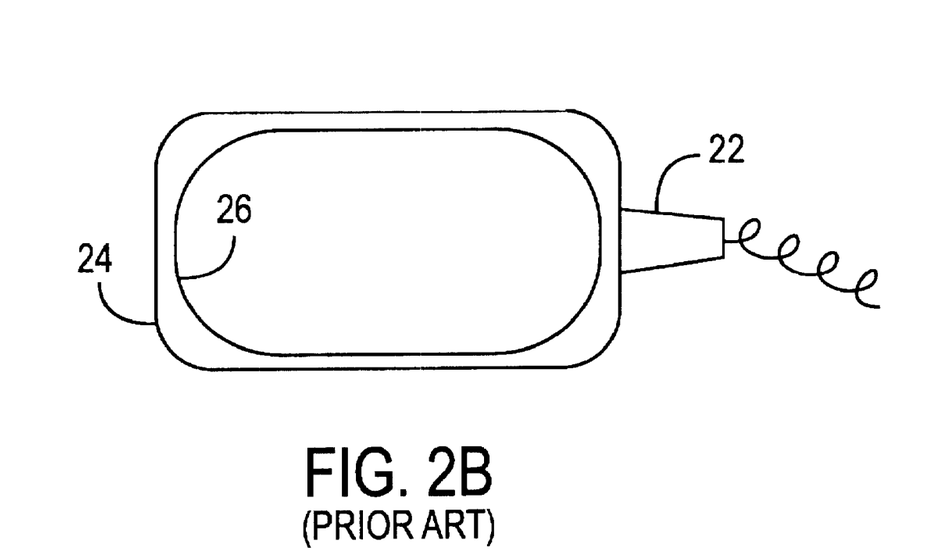

FIGS. 2A and 2B show a conventional reusable paddle 20 which is one of two that are used instead of the pads 10 shown in FIG. 1. The paddles 20 include a handle 22, which the caregiver grips in order to place and maintain the paddle 20 at a predetermined location on the patient, and a conductor plate 24 through which the defibrillation shock is applied. In order to reduce the impedance caused by dry skin or other factors related to the patient, a conductive medium 26 such as a gel is normally placed on the conductor plate 24.

An advantage of using paddles 20 is that they are reusable. As such, the same pair of paddles 20 can be used again so long as the conductive medium 26 is removed and the paddles 20 are decontaminated and cleaned after use. However, the paddles 20 have drawbacks in that, in order to administer defibrillation, the caregiver must press the paddles 20 onto the patient. By having the caregiver be in close proximity to the patient, the caregiver is exposed to a shock hazard during defibrillation. In addition, the use of the conductive medium 26 creates a mess both on the paddles and the patient, increases the chance of shock to the caregiver, and makes the paddles 20 difficult to clean and decontaminate. Further, the paddles 20 are relatively large and heavy in comparison to the pads 10. Lastly, since the paddles 20 are not attached to the patient, the paddles 20 cannot be used or are not practical for use in ECG monitoring, for external cardiac pacing, for cardioversion where pacing is performed, or for automatic ECG interpretive algorithms defibrillators (automatic external defibrillators) that indicate when a shock is to be delivered because these functions require the electrodes to be in extended contact and a motion free relationship with the patient. An example of the reusable paddles 20 is the part no. M4746A produced by Agilent Technologies.

For additional information on the use and placement of pads 10 and paddles 20 in conjunction with a defibrillator 1 having monitoring capabilities, reference is made to the Agilent M4735A Heartstream XL Defibrillator/Monitor User's Guide (Agilent Technologies) (Edition 1, September, 2000), which is incorporated herein by reference.

SUMMARY OF THE INVENTION

According to an embodiment of the present invention, a paddle for use with a defibrillator includes an applicator, a pad portion electrically connected to the applicator and having a conductive medium removably encased in the pad portion, and an electrical contact electrically connected to one of the applicator or the pad portion, the electrical contact being exposed while the conductive medium is encased in the pad portion.

According to another embodiment of the present invention, an applicator for use with an adhesive pad to form a paddle for use with a defibrillator includes a main body having a bottom, a connector on the bottom to electrically and mechanically attach the main body to the adhesive pad along a primary electrical path between a patient, the main body and the defibrillator, a handle attached to the main body, and an electrical contact attached to the main body to form a secondary electrical path between the patient, the main body and the defibrillator.

According to still another embodiment of the present invention, a pad portion for use with an applicator to form a paddle for use with a defibrillator includes a backing having a top and a bottom, a connector attached to the top to form a mechanical and electrical connection to the applicator, a conductive medium attached to the bottom, a lid to encase the conductive medium, and an electrical contact disposed on the lid to provide an electrical pathway to the applicator when the conductive medium is encased by the lid.

According to yet another embodiment of the present invention, a method of using a paddle with a defibrillator includes attaching a pad portion to an applicator portion to form the paddle, the pad portion having a conductive medium encased by a lid, assessing a condition of a patient by forming an electrical pathway between the defibrillator and the patient using an electrical contact disposed on the lid or the applicator, and removing the lid to connect the paddle to the patient to form another electrical pathway between the defibrillator and the patient.

According to a further embodiment of the present invention, a paddle for use with a defibrillator includes an applicator having a flexible plate that shapes to a curvature of a patient, a handle attached to a top of the flexible plate, and an applicator connector disposed on a bottom of the flexible plate; a pad portion electrically connected to the applicator, having a flexible backing that is shaped by the flexible plate, a pad portion connector disposed on a top of the flexible backing to form an electrical and mechanical connection to the applicator connector, a lid attached to the flexible backing, and an adhesive conductive medium attached to a bottom of the flexible backing and removably encased by the lid, the adhesive conductive medium comprising a flexible conductor disposed between an adhesive layer and the flexible backing; and an electrical contact disposed on the lid electrically connected to the pad portion, the electrical contact being exposed while the adhesive conductive medium is encased by the lid so as to send signals to said applicator through the conductive medium.

According to a still further embodiment of the present invention, a paddle for use with a defibrillator includes an applicator having a flexible plate that shapes to a curvature of a patient, a handle attached to a top of the flexible plate, and an applicator connector disposed on a bottom of the flexible plate; a pad portion electrically connected to the applicator, having a flexible backing that is shaped by the flexible plate, a pad portion connector disposed on a top of the flexible backing to form an electrical and mechanical connection to the applicator connector, an adhesive conductive medium attached to a bottom of the flexible backing, the adhesive conductive medium comprising a flexible conductor disposed between an adhesive layer and the flexible backing, and the adhesive conductive medium being shaped to be removably encased by a bag; and an electrical contact disposed on the flexible plate adjacent to the applicator connector so as to form an additional electrical pathway between the defibrillator and the applicator while the pad portion is not connected to said applicator.

According to a yet further embodiment of the present invention, a paddle for use with a defibrillator includes an applicator having a flexible plate that shapes to a curvature of a patient, a handle attached to a top of the flexible plate, and an applicator connector disposed on a bottom of the flexible plate; a pad portion electrically connected to the applicator, having a flexible backing that is shaped by the flexible plate, a pad portion connector disposed on a top of the flexible backing to form an electrical and mechanical connection to the applicator connector, an adhesive conductive medium attached to a bottom of the flexible backing, the adhesive conductive medium comprising a flexible conductor disposed between an adhesive layer and the flexible backing, and a layer removably encasing the adhesive conductive medium; and an electrical contact disposed on the flexible plate adjacent to the handle so as to form an additional electrical pathway between the defibrillator and the applicator while the adhesive conductive medium is encased by the layer.

BRIEF DESCRIPTION OF THE DRAWINGS

These and other objects and advantages of the invention will become apparent and more readily appreciated from the following description of the preferred embodiments, taken in conjunction with the accompanying drawings of which.

DETAILED DESCRIPTION OF THE PREFERRED EMBODIMENTS

Reference will now be made in detail to the present preferred embodiments of the present invention, examples of which are illustrated in the accompanying drawings, wherein like reference numerals refer to the like elements throughout. The embodiments are described below in order to explain the present invention by referring to the figures.

Figure 3:
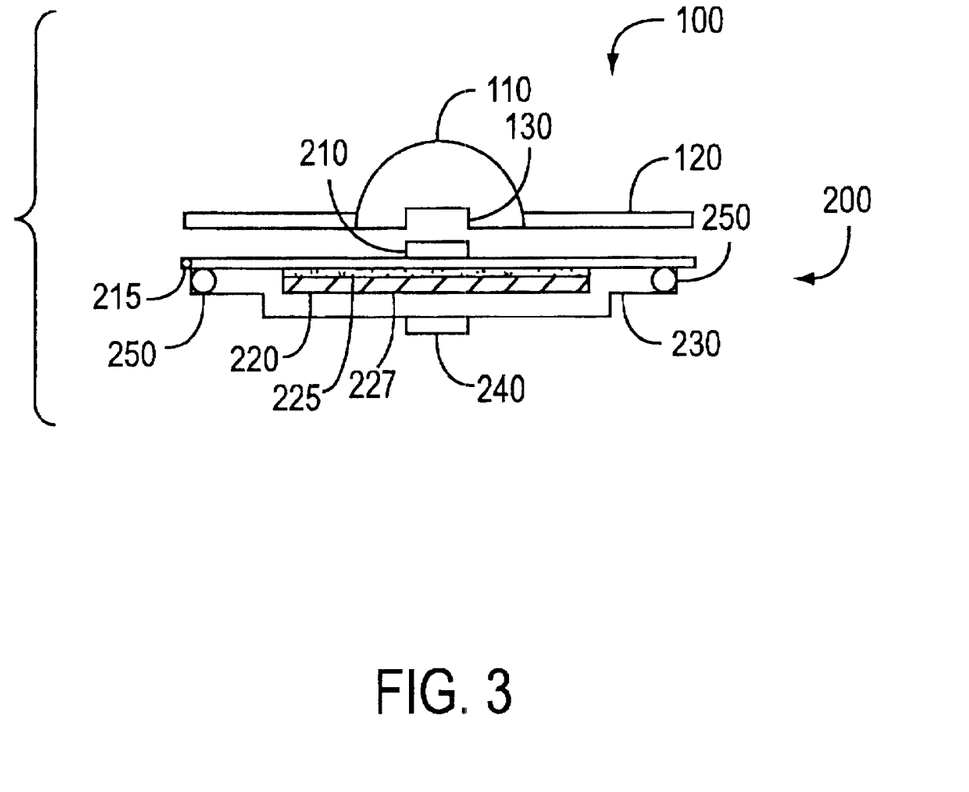
FIG. 3 is a cross-sectional side view of a hands-free paddle according to an embodiment of the present invention.

FIG. 3 shows a hands-free paddle according to an embodiment of the present invention. The hands-free paddle includes a reusable portion 100 (i.e., an applicator) and a pad 200. The reusable portion 100 includes a handle 110, an applicator plate 120, and a connector receptacle 130 within the handle 110. The handle 110 can be removably attached or permanently attached to the applicator plate 120.

The reusable portion 100 can be made of materials similar to those used in conventional paddles 20, such as the M4746A external paddle produced by Agilent Technologies. The reusable portion 100 is preconnected to a defibrillator using leads (not shown).

The pad 200 includes a connector 210, which is received by the connector receptacle 130 in order to connect, both electrically and mechanically, the pad 200 to the defibrillator (not shown) through the reusable portion 100. The connector 210 is attached to a top of a plate 215. A conductive medium 220 is disposed on a bottom of the plate 215. The conductive medium 220 includes both a flexible conductor 225 and a hydrogel adhesive 227 similar to those used in the single-use pads 10 such as the Heartstream pads produced by Agilent Technologies (part no. M3713A). The flexible conductor 225 is sandwiched between the hydrogel adhesive 227 and the plate 215. As such, when used, the reusable portion 100 is connected to the pad 200 allowing a defibrillation shock to be applied through the conductive medium 220 to the patient. Further, the adhesive nature of the conductive medium 220 allows for extended contact and a motion-free relationship with the patient as to allow for the caregiver, in addition to providing defibrillation, to provide electrocardiograph (ECG) monitoring, external cardiac pacing, and cardioversion.

While not shown, it is understood that the conductive medium 220 need not be adhesive in all instances, such as when hands-free operation is not required, and the adhesive 227 is not always required in all instances, such as when an adhesive is later applied or is not needed in order to accomplish a hands-free operation.

In order to prevent the conductive medium 220 from drying out and being contaminated prior to use, a lid 230 encases the conductive medium 220. The lid 230 includes a seal 250 disposed between the lid 230 and the plate 215 to encase the conductive medium 220. The lid 230 is semi conductive and includes a quick look contact 240 attached to a bottom of the lid 230. In the alternative, the lid 230 includes a lead extending from the quick look contact 240 through the lid 230 and removably attached to the conductive medium 220. The quick look contact 240 is electrically connected to the connector 210 through the lid 230 and the conductive medium 220. Since the quick look contact 240 is external to the lid 230, the caregiver can obtain a quick look ECG reading without removing the lid 230 and exposing the conductive medium 220 so as to require the pad 200 to be thrown away. As such, the quick look contact 240 forms a second electrical path between the patient, the reusable portion 100, and the defibrillator.

When in use, the caregiver connects the hands-free paddle to a defibrillator using leads (not shown), and connects the pad 200 to the reusable portion 100 by inserting the connector 210 into the connector receptacle 130. While not shown, it is generally understood that the connector 210 could be located on the handle 110, with the connector receptacle 130 being located in the plate 215.

Once connected, the caregiver can determine if a quick look of the patient's condition is warranted. To perform a quick look, the caregiver makes a temporary and abbreviated contact to the patient to obtain a heart rhythm. If such a quick look is warranted, the caregiver applies the quick look contact 240 to the patient in order to obtain the desired reading. While shown as being relatively stiff, it is understood that the lid 230 can be flexible so long as the lid 230 does not permanently adhere to the conductive medium 220. Further, the lid 230 is able to be wiped clean such that, if a quick look is performed and no further use of the hands-free paddle is required, the lid 230 can be wiped clean without having to be disposed of as is the case with the conventional pads 10 shown in FIG. 1.

If defibrillation therapy is required, or if an electrode that is motionless in relation to the patient is required for monitoring, the lid 230 is removed to expose the conductive medium 220. The hands-free paddle is then adhered to the patient, which allows the caregiver to no longer be in contact with the hands-free paddle. In order to better adhere the hands-free paddle to the patient, the applicator plate 120 should be somewhat stiff, but needs to be able to conform to the shape of a patient's body to increase the amount of the conductive medium 220 in contact with the patient. Thus, the applicator plate 120 could be stiff and curved, or as shown, is flexible or has a flexible portion such as a padded portion to allow the caregiver to mold the hands-free paddle to the shape of the patient. In this way, the caregiver uses the applicator plate 120 to evenly adhere the conductive medium 220 to the patient.

After use, the pad 200 is removed from the patient and disposed of. The reusable portion 100 is cleaned, but is otherwise immediately available to be connected to a new pad 200 as need be.

Figure 4:
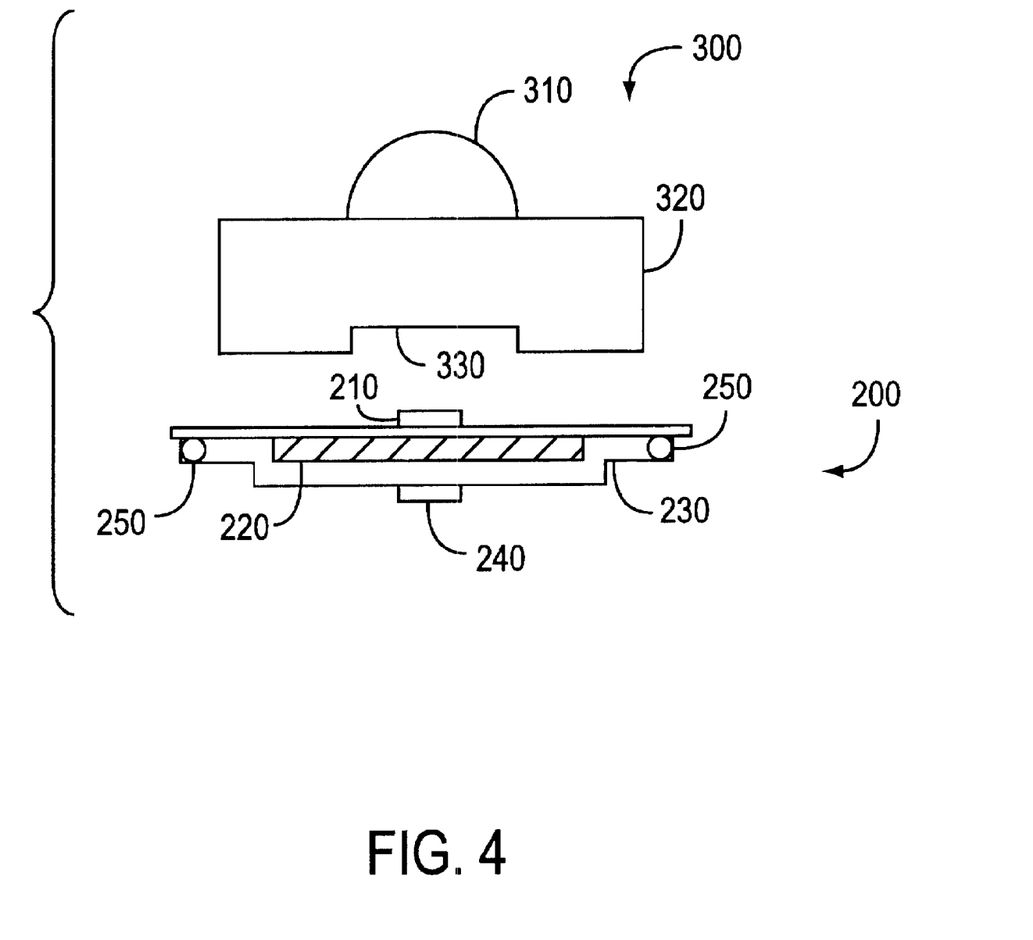
FIG. 4 is a cross-sectional side view of a hands-free paddle according to another embodiment of the present invention.

FIG. 4 shows a hands-free paddle according to another embodiment of the present invention, where the reusable portion 300 has a thickened applicator plate 320 as compared to the applicator plate 120 shown in FIG. 3 as to be comparatively rigid. The reusable portion 300 also has a handle 310 connected to the applicator plate 320, and a connector receptacle 330 within the applicator plate 320 to attach to the connector 210 of the pad 200 shown in FIG. 3. The thickened applicator plate 320 can also include a bendable portion as to better conform to a shape of the patient. The handle 310 can be removably attached or permanently attached to the applicator plate 320.

Figure 5:
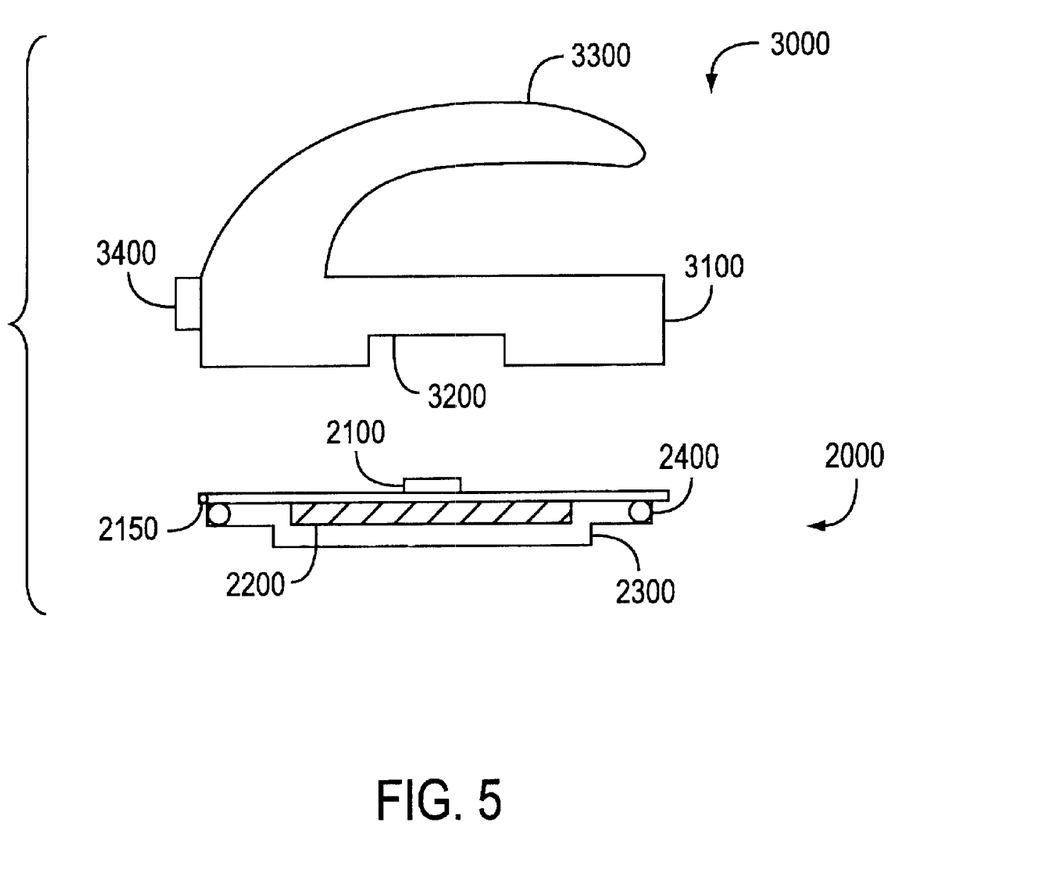
FIG. 5 is a cross-sectional side view of a hands-free paddle having a handle and a quick look contact on the reusable portion according to yet another embodiment of the present invention.

FIG. 5 shows a hands-free paddle according to yet another embodiment of the present invention. The reusable portion 3000 contains a handle 3300 that extends down to approximately a front side of an applicator plate 3100. The handle 3300 can be removably attached or permanently attached to the applicator plate 3100. A quick look contact 3400 is located at the front of the applicator plate 3100. As such, in order to perform a quick look on the patient's condition, a pad 2000 does not have to be connected to the reusable portion 3000 as does the pad 200 shown in FIG. 3. Instead, the pad 2000 need only be connected to the reusable portion 3000 if therapy beyond the quick look is to be provided. The reusable portion 3000 is connected to the pad 2000 using a connector 2100 and a connector receptacle 3200, which provides an electrical and mechanical connection between the reusable portion 3000 and the pad 2000.

The connector 2100 is attached to a top of a plate 2150. A conductive medium 2200 including a flexible conductor and an adhesive hydrogel is disposed on a back of the plate 2150. A lid 2300 is connected to the plate 2150 using a seal 2400. In this way, the conductive medium 2200 does not dry out or otherwise lose its adhesive properties by exposure prior to use (i.e., when the lid 2300 is removed).

While not shown, it is understood that pad 200 shown in FIG. 3 could be connected to the reusable portion 3000, providing a second quick look contact 240 in addition to the quick look contact 3400.

In contrast to the embodiments of the present invention shown in FIGS. 4 and 5, since the pad 2000 is not used to provide the quick look as is the pad 200, the lid 2300 does not require an integral conductive area electrically connected to the conductive medium 2200 such as the quick look contact 240 shown in FIGS. 4 and 5. Thus, the lid 2300 does not have to be semi conductive as does the lid 230 shown in FIGS. 3 and 4.

Figure 6:
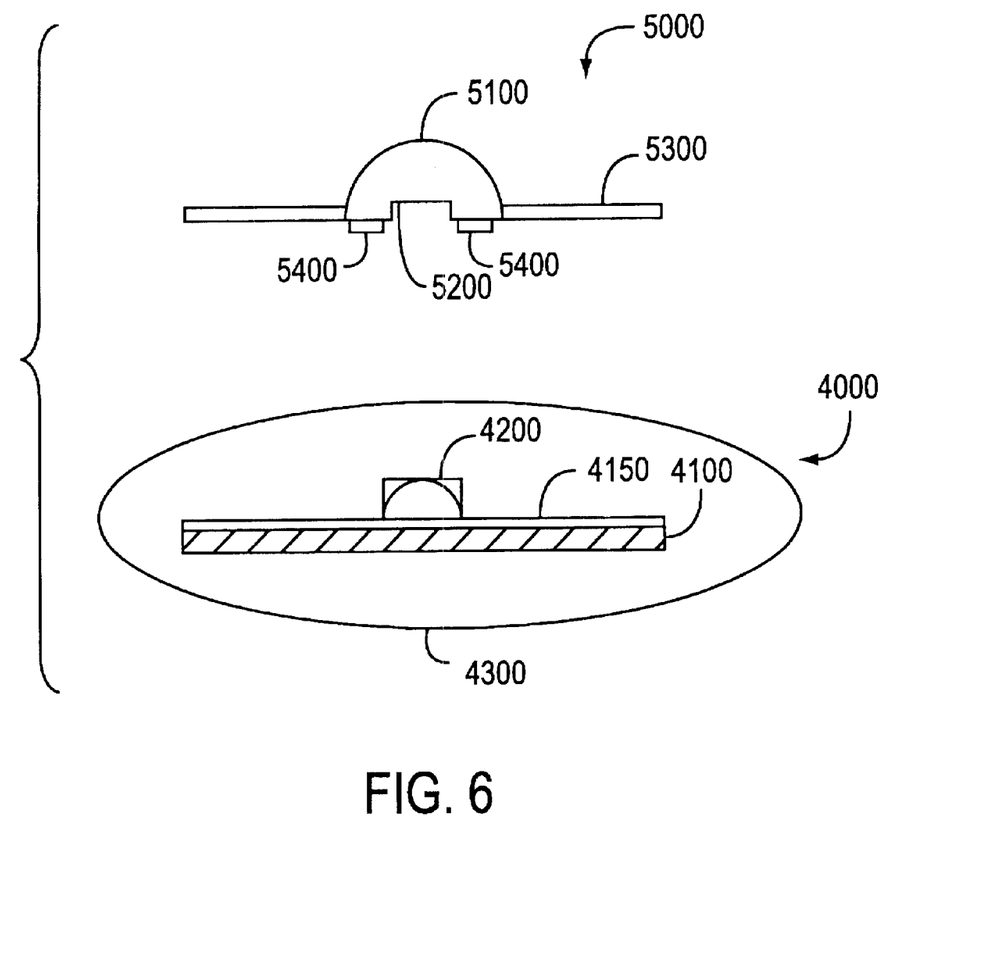
FIG. 6 is a cross-sectional side view of a hands-free paddle having a quick look contact on the reusable portion for use with a pad sealed in a bag according to a further embodiment of the present invention.

FIG. 6 shows a hands-free paddle according to a further embodiment of the present invention. The reusable portion 5000 includes a handle 5100 removably or permanently connected to an applicator plate 5300. A connector receptacle 5200 is located within the handle 5100. A quick look contact 5400 is located underneath the handle 5100 and adjacent to the connector receptacle 5200. In this way, if a caregiver needs to perform a quick look to obtain an ECG, the reusable portion 5000 can be used alone.

Where additional monitoring or therapy capabilities are required to obtain a passive reading from or inject electricity into the patient, a pad 4000 is connected to the reusable portion 5000 using a connector 4200, which connects to the connector receptacle 5200. The pad 4000 further includes a plate 4150. The connector 4200 is attached to a top of the plate 4150, and a conductive medium 4100 is attached to a bottom of the plate 4150. The conductive medium 4100 includes a flexible conductor and a hydrogel adhesive. The conductive medium 4100, the plate 4150, and the connector 4200 are sealed in a bag 4300 to prevent the conductive medium 4100 from drying out or otherwise losing its adhesive properties. By using the bag 4300, the pad 4000 is generally not connected to the reusable portion 5000 without removing the bag 4300. However, it is generally understood that the bag 4300 need not be removed prior to attaching the pad 4000 to the reusable portion 5000. By using a less complicated structure than is found with the pads 200 and 2000 shown in FIGS. 3 and 5, the cost of production is further reduced.

While not shown, it is understood that the bag 4300 need only cover the conductive medium 4100.

According to the hands-free paddle of the present invention, the caregiver is able to obtain a quick look to assess the patient's condition, and is also able to administer hands-free defibrillation therapy to the patient so as to combine the advantages of the conventional paddles and pads without the accompanying limitations. In addition, since the leads from the defibrillator are attached to the reusable portion/the applicator, the production cost for the pads is reduced in comparison to the production cost for the pads, and also have the benefit of providing a simple mechanism for testing the conductive medium within the pad while encased as compared to the mechanisms required for testing encased conventional pads.

Further, since the hands-free paddle according to the present invention can be attached to the patient by the pad, the hands-free paddle can perform the four basic functions of a cardiac defibrillator including defibrillation, ECG monitoring, external cardiac pacing, and cardioversion while still having a reusable preconnected component. At the same time, the hands-free paddles are easier to clean and decontaminate, and are relatively smaller and lighter than conventional paddles.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A paddle for use with a defibrillator, comprising:
   an applicator;
   a pad portion adapted to be electrically connected to said applicator and having a conductive medium removably encased by a lid; and
   an electrical contact electrically connected to at least one of said applicator and said pad portion, said electrical contact being exposed while the conductive medium is encased in said pad portion.
2. The paddle of claim 1, wherein said applicator has a plate that shapes said pad portion to a curvature of a patient.
3. The paddle of claim 2, wherein the plate has a portion that curves to the curvature of the patient.
4. The paddle of claim 2, wherein the plate is flexible.
5. The paddle of claim 1, wherein said pad portion further comprises a backing to which the conductive medium is attached, and said electrical contact is attached to the lid.
6. The paddle of claim 5, wherein said applicator further comprises a plate to which the backing is attached, the plate to shape the backing and the conductive medium to a curvature of a patient.
7. The paddle of claim 5, wherein the conductive medium further comprises an adhesive layer and a conductor, the conductor being disposed between the adhesive layer and the backing.
8. The paddle of claim 7, wherein said electrical contact sends signals to said applicator through the conductive medium.
9. The paddle of claim 1, wherein said electrical contact is attached to a side of said applicator.
10. The paddle of claim 9, wherein said applicator further comprises a handle, and the side is adjacent said pad portion and the handle.
11. The paddle of claim 9, wherein said pad portion is attached to the side.
12. The paddle of claim 9, wherein the lid comprises a bag to removably encase the conductive medium.
13. The paddle of claim 9, wherein said pad portion is not attached to the side.
14. The paddle of claim 13, wherein: said applicator further comprises
    a handle,
    a bottom side opposite said pad portion, and
    a front side adjacent the bottom side; and the side to which the electrical contact is attached comprises the front side.
15. An applicator for use with an adhesive pad to form a paddle for use with a defibrillator, comprising:
    a main body comprising
        a bottom side, and
        a connector on the bottom side adapted to electrically and mechanically attach said main body to the adhesive pad along a primary electrical path between a patient, said main body, and the defibrillator;
    a handle attached to said main body; and
    an electrical contact attached to said main body to form a secondary electrical path between the patient, said main body, and the defibrillator.
16. The applicator of claim 15, wherein said electrical contact is disposed adjacent the connector on the bottom side.
17. The applicator of claim 15, wherein said electrical contact is not disposed on the bottom side.
18. The applicator of claim 17, wherein said electrical contact is disposed on a side adjacent the bottom side.
19. The applicator of claim 18, wherein said handle is attached to said main body at approximately a front side of said main body adjacent to the bottom side, and said electrical contact is disposed on the front side.
20. A pad portion for use with an applicator to form a paddle for use with a defibrillator, comprising:
    a backing having a top side and a bottom side;
    a connector attached to the top side adapted to form a mechanical and electrical connection to the applicator;
    a conductive medium attached to the bottom side;
    a lid to encase said conductive medium; and an electrical contact disposed external on said lid to provide an electrical pathway between a patient and the defibrillator through the applicator when said conductive medium is encased by said lid.

21. The pad portion of claim 20, wherein said conductive medium comprises an adhesive layer and a conductor disposed between said backing and the adhesive layer.

22. The pad portion of claim 21, wherein said backing is flexible to adapt to a curvature of the patient.

23. A paddle for use with a defibrillator, comprising:
an applicator comprising:
  a plate having a top side and a bottom side that shapes to a curvature of a patient,
  a handle attached to the top side of the plate, and
  an applicator connector disposed on the bottom side of the plate;
a pad portion adapted to be electrically connected to said applicator, comprising
  a flexible backing that is shaped by the plate,
  a pad portion connector disposed on a top side of the flexible backing adapted to form an electrical and mechanical connection to the applicator connector,
  a lid attached to the flexible backing, and
  an adhesive conductive medium attached to a bottom side of the flexible backing and removably encased by the lid, the adhesive conductive medium comprising a flexible conductor disposed between an adhesive layer and the bottom side of the flexible backing; and
an electrical contact disposed on the lid electrically connected to said pad portion, said electrical contact being exposed while the adhesive conductive medium is encased by the lid so as to send signals to said applicator through the adhesive conductive medium.

24. A paddle for use with a defibrillator, comprising:
an applicator comprising:
  a plate having a top side and a bottom side that shapes to a curvature of a patient,
  a handle attached to the top side of the plate, and
  an applicator connector disposed on the bottom side of the plate;
a pad portion adapted to be electrically connected to said applicator, comprising
  a flexible backing that is shaped by the plate,
  a pad portion connector disposed on a top side of the flexible backing adapted to form an electrical and mechanical connection to the applicator connector,
  an adhesive conductive medium attached to a bottom side of the flexible backing, the adhesive conductive medium comprising a flexible conductor disposed between an adhesive layer and the bottom side of the flexible backing, the adhesive conductive medium being shaped to be encased by a bag; and
an electrical contact disposed on the plate adjacent to the applicator connector so as to form an additional electrical pathway between the defibrillator and said applicator while said pad portion is not connected to said applicator.

25. A paddle for use with a defibrillator, comprising:
an applicator comprising:
  a plate having a top side and a bottom side that shapes to a curvature of a patient,
  a handle attached to the top side of the plate, and
  an applicator connector disposed on the bottom side of the plate;
a pad portion adapted to be electrically connected to said applicator, comprising
  a flexible backing that is shaped by the plate,
  a pad portion connector disposed on a top side of the flexible backing adapted to form an electrical and mechanical connection to the applicator connector,
  an adhesive conductive medium attached to a bottom side of the flexible backing, the adhesive conductive medium comprising a flexible conductor disposed between an adhesive layer and the bottom side of the flexible backing, and
  a layer removably encasing the adhesive conductive medium; and
an electrical contact disposed on the plate adjacent to the handle so as to form an additional electrical pathway between the defibrillator and said applicator while the adhesive conductive medium is encased by the layer.

26. A method of using a paddle with a defibrillator, comprising:
attaching a pad portion to an applicator to form the paddle, the pad portion having a conductive medium encased by a lid;
assessing a condition of a patient by forming an electrical pathway between the defibrillator and the patient using an electrical contact disposed on at least one of the lid or the applicator and an additional electrode; and
removing the lid to connect the paddle to the patient to form another electrical pathway between the defibrillator and the patient using the paddle and the additional electrode.

27. The method of claim 26, wherein the electrical contact is disposed on the lid.

28. The method of claim 26, wherein the electrical contact is disposed on the applicator.

29. The method of claim 26, wherein said assessing the condition of the patient comprises forming an electrical pathway while the conductive medium is encased by the lid.

30. The method of claim 26, wherein the lid comprises a bag encasing the conductive medium.

31. The method of claim 30, wherein said removing the lid is before said attaching the pad portion to the applicator.

32. The method of claim 26, further comprising removing the pad portion from the applicator after said removing the lid.

33. The method of claim 26, further comprising adhering the paddle to the patient using an adhesive layer of the conductive medium after said removing the lid.

34. The method of claim 33, further comprising removing the pad portion from the applicator after said adhering the paddle.

* * * * *